United States Patent [19]

Dietze et al.

[11] Patent Number: 5,393,391
[45] Date of Patent: Feb. 28, 1995

[54] ELECTRODE ARRANGEMENT FOR THE ELECTROCHEMICAL ANALYSIS OF ELECTROLYTIC COMPONENTS OF A LIQUID

[75] Inventors: Werner Dietze, Tutzing; Hans-Peter Haar, Weilheim; Horst Herrmann, Bernried; Dieter Knoll, Kronberg; Wolfgang Reiser, Seeshaupt, all of Germany

[73] Assignee: Boehringer Mannheim GmbH, Mannheim, Germany

[21] Appl. No.: 728,768

[22] Filed: Jul. 8, 1991

Related U.S. Application Data

[63] Continuation of Ser. No. 499,227, Mar. 26, 1990, abandoned, which is a continuation of Ser. No. 291,241, Dec. 28, 1988, abandoned, which is a continuation of Ser. No. 591,770, Mar. 21, 1984, abandoned.

[30] Foreign Application Priority Data

Apr. 11, 1983 [DE] Germany .......................... 3312923

[51] Int. Cl.⁶ .............................................. G01N 27/30
[52] U.S. Cl. .................................. 204/153.1; 204/403; 204/409; 204/415; 204/435
[58] Field of Search ................. 128/635; 204/403, 409, 204/412, 414, 415, 419, 420, 435, 416, 153.1, 153.12, 153.15, 153.16, 153.17

[56] References Cited

U.S. PATENT DOCUMENTS

| | | | |
|---|---|---|---|
| 3,681,255 | 8/1972 | Wilfore | 204/153.1 X |
| 3,882,012 | 5/1975 | Dickinson et al. | 204/412 |
| 3,890,201 | 6/1975 | Cady | 195/127 |
| 4,053,381 | 10/1977 | Hamblen et al. | 204/416 |
| 4,072,578 | 2/1978 | Cady et al. | 204/403 X |
| 4,184,936 | 1/1980 | Paul et al. | 204/416 X |
| 4,214,968 | 7/1980 | Battaglia et al. | 204/435 X |
| 4,225,410 | 9/1980 | Pace | 204/412 |
| 4,235,688 | 11/1980 | Sudrabin et al. | 204/435 |
| 4,271,119 | 6/1981 | Columbus | 204/416 X |
| 4,282,079 | 8/1981 | Chang et al. | 204/435 X |
| 4,302,313 | 11/1981 | Columbus | 204/435 X |
| 4,310,399 | 1/1982 | Columbus | 204/409 |
| 4,318,884 | 3/1982 | Suzuki | 422/100 X |
| 4,318,885 | 3/1982 | Suzuki et al. | 422/63 X |
| 4,457,184 | 7/1984 | Shiono | 422/100 X |

FOREIGN PATENT DOCUMENTS 0010457 11/1982 European Pat. Off. .

OTHER PUBLICATIONS

C. Cammann, "Working with Ion-Selective Electrode", Springer-Verlag, Berlin, 1979 pp. 49-92.

*Primary Examiner*—Nam Nguyen
*Attorney, Agent, or Firm*—Felfe & Lynch

[57] ABSTRACT

The present invention provides an electrode arrangement for the electrochemical analysis of components of a liquid, having a base body (7; 53; 85; 103; 139; 155; 175; 193), made of an insulating material with at least one measurement electrode (21; 57; 89; 111; 143; 157; 195) held on the base body, adapted to be brought into phase boundary contact with the liquid to be analysed, said measurement electrode being selective for a predetermined kind of ion in the liquid, and with at least one reference electrode (19; 55; 87; 109; 141; 153; 173; 197; 199) held on the base body and adapted to be brought into phase boundary contact, together with the measurement electrode, with the liquid, wherein the base body carries a removable closure part (45; 61; 91; 107; 137; 163; 187; 203) which, together with the base body, forms a closed hollow chamber (11; 52; 86; 104; 135; 159; 177; 201), the closed hollow chamber containing a standard electrolyte, especially one containing the predetermined kind of ion, defining, with the ion-selective measurement electrode, a predetermined half cell potential, said standard electrolyte being in phase boundary contact not only with the or each measurement electrode but also with the or each reference electrode.

20 Claims, 5 Drawing Sheets

ELECTRODE ARRANGEMENT FOR THE ELECTROCHEMICAL ANALYSIS OF ELECTROLYTIC COMPONENTS OF A LIQUID

This application is a continuation of application Ser. No. 499,227, filed Mar. 26, 1990, which is a continuation of application Ser. No. 291,241, filed Dec. 28, 1988, which is a continuation of application Ser. No. 591,770, filed Mar. 21, 1984, all abandoned.

The present invention is concerned with an electrode arrangement for the electrochemical analysis of electrolytic components of a liquid, having a base body of insulating material with at least one measurement electrode on the base body which is adapted to be brought into phase boundary contact with the liquid, the measurement electrode or electrodes being selective for a predetermined kind of ion in the liquid, and with at least one reference electrode on the base body which is adapted to be brought, together with the measurement electrode, into phase boundary contact with the liquid.

With the help of such electrode arrangements, in clinical chemistry there is measured, for diagnostic purposes, the activity or concentration of ions in body fluids, especially in blood and urine. Between the reference electrode and the ion-selective measurement electrode connected electrolytically with the reference electrode via the body fluid, there occurs a voltage which is a measure for the concentration of the kind of ion to be measured and which can be measured by means of a high-ohmic voltage measurement apparatus. The measurement electrode and reference electrode commonly wetted by the body fluid hereby form the two half cells of an electrochemical cell.

Ion selective measurement electrodes are known, for example, from the book "Working with ion-selective electrodes" by Carl Cammann, pub. Springer-Verlag, Berlin, 1979, pages 49 to 92. The ion-selective measurement electrode produces a half cell potential which, within the desired measurement exactitude, depends sufficiently selectively only upon the kind of ions in the liquid to be analysed. They can, for example, include an electrode chamber filled with a lead-off electrolyte, which chamber is separated from the liquid to be analysed by an ion-selective membrane. An electron-conducting lead-off element dips into the lead-off electrolyte. Instead of the membrane, there can, for example, also be used selective ion-conductive glasses. Other known ion-selective measurement electrodes include solid body electrodes, especially of pressed powder or single crystals, which, besides ion-conductability properties, can also have electron conductability properties.

Reference electrodes are also known, for example from the above-mentioned book, pages 31 to 48. The reference electrode produces a half cell potential which, within the period of time available for the analysis, is a predetermined value which is as constant as possible and is independent of the liquid to be analysed. During the course of 1 minute, the reference potential should not vary more than $\pm 50$ $\mu V$. Similarly to the measurement electrodes, they include an electron-conducting lead-off element which dips into a reference electrolyte. The reference electrolyte contains, in a fixed concentration, a kind of ion which, because of a reversible electrochemical reaction, produces with the lead-off element a constant potential, independently of the liquid to be analysed with which the reference element is in electrolytic contact. In the case of the reaction system consisting of lead-off element and reference electrolyte, it can be, for example, a silver/silver chloride system. Thallium amalgam/thallium-I chloride systems can also be used. Other reference electrodes are based on the principle of ion-selective electrodes, the reference electrolyte thereby containing the kind of ion to be analysed in fixed activity.

The reference electrolyte of the reference electrode is generally separated by a membrane or some other kind of electrolyte bridge from the material to be measured or the liquid to be analysed in order, at least during the period of the measurement, to prevent concentration changes and thus mixings leading to measurement errors. There can be used for example, capillary constructions between the material to be measured and the electrolyte of the reference electrode.

An electrode arrangement of the above-described type is known from European Patent Specification No. 0010457. On to an insulating body there are applied, at a distance from one another, two ion-selective electrodes wettable via separate supply canals of the insulating body. The supply canals are connected with one another by a transversely running capillary slot. The membranes of the ion-selective electrodes provided with solid contacts, the supply canals, as well as the capillary slot connecting the supply canals, are symmetrically arranged to give a symmetrical plane running between the electrodes. For the measurement of the ion activity, one of the supply canals is supplied with the body fluid to be analysed, for example blood, and the other supply canal is simultaneously supplied with a reference electrolyte liquid of known ion activity. The suction action of the capillary canal brings about the electrolyte connection between the electrodes.

This known electrode arrangement is a disposable part which can only be used once. The electrodes are, in the case of supplying with the body fluid to be analysed or with reference electrolyte, first wetted immediately before commencement of the measurement. Since the electrodes require a certain period of time for conditioning after the first wetting and, on the other hand, because of the direct contacting of the liquid to be analysed and the reference electrolyte in the capillary slot, the period of time available for the measurement is limited and, in individual cases, measurement errors can occur because the degree of conditioning of the electrodes cannot be exactly predicted. Since the suction properties of the capillary slot are exhausted after a single wetting, it is not possible to carry out a calibration measurement with a standard electrolyte with a known concentration of the kind of ions to be analysed before carrying out the actual analytical measurement.

It is an object of the present invention to provide an electrode arrangement in the manner of a disposal part for carrying out a single analytical measurement, which electrode arrangement is simple to handle and economic to produce and, at the same time, quickly provides precise results. According to a first main aspect of the present invention, it is to permit, on the one hand, sufficient preconditioning of its electrodes and, on the other hand, a calibration measurement preceding the analytical measurement. Furthermore, according to a second main aspect of the present invention, there is provided a construction of a reference electrode which is characterised by an especially simple and economic production and, nevertheless, has an excellent stability and makes possible a short adjustment time. This second main aspect of the present invention is especially of importance in conjunction with the first main aspect but is also of importance independently from the same.

Thus, according to the first main aspect of the present invention, there is provided an electrode arrangement for the electrochemical analysis of components of a liquid, having a base body made of an insulating material with at least one measurement electrode held on the base body, adapted to be brought into phase boundary contact with the liquid to be analysed, said measurement electrode being selective for a predetermined kind of ion in the liquid, and with at least one reference electrode held on the base body and adapted to be brought into phase boundary contact, together with the measurement electrode, with the liquid, wherein the base body carries a removable closure part which together with the base body, forms a closed hollow chamber, the closed hollow chamber containing a standard electrolyte, especially one containing the predetermined kind of ion, defining, with the ion-selective measurement electrode, a predetermined half cell potential, said standard electrolyte being in phase boundary contact not only with the or each measurement electrode but also with the or each reference electrode.

Such an electrode arrangement is, in the manner of a disposable article, only intended for a single analytical measurement. The sample chamber is provided with the standard electrolyte by the manufacturer and is closed. Since the electrodes are constantly wetted with the standard electrolyte, they are preconditioned so that the electrode arrangement is immediately ready for use. The standard electrolyte used for the preconditioning permits, before the actual analytical measurement, the carrying out of a calibration measurement, for example while the hollow chamber is still closed. For the analytical measurement, the closure part is removed and the standard electrolyte removed before a sample of the liquid to be analysed is introduced. The standard electrolyte is preferably a liquid, the viscosity of which can be considerably increased by physico-chemical processes, for example by conversion into a gel form, by thickening with a silicon dioxide thickening agent or by take up in a hydrophilic synthetic resin, for example polyvinyl alcohol.

Under special circumstances, a reference electrode can be used which does not have reference electrolytes which can mix with the sample liquids, one example of this being a hydrogen normal electrode. However, in the cases of use which are important for clinical chemistry, especially for the investigation of blood, as a rule, a reference electrode of the type hereinbefore already mentioned must be used in which a reference electrolyte, together with a lead-off contact element, provides for a stable half cell potential. In this case, the reference electrolyte is preferably a solution which contains the same kinds of ions as the standard electrolyte in the same activity. In this way, it is achieved that exchange of the ions between the reference electrolyte and the standard electrolyte present in the hollow chamber does not change the activity in both solutions. In the case of the present invention, this would not be tolerated because the electrode arrangement according to the present invention, constructed as a disposable part, must be capable of being stored for a long time with the prepacked standard electrolyte. This preferred measure is of importance not only for the case in which, between the hollow chamber and the reference electrolyte, there is present an electrolyte bridge but also for the case in which, as is hereinafter described in more detail, the lead-off contact element of the reference electrode projects directly into the hollow chamber and this, so long as it is closed by the removable closure part, is filled with an electrolyte solution which has not only reference but also standard electrolyte properties.

Especially preferably, the reference electrolyte and the standard electrolyte are of identical composition. For this case, in the following they are also referred to as standard/reference electrolyte.

In the case of the measurement electrodes, too, constructions are also known which do not require a lead-off electrolyte. However, especially preferred are the hereinbefore mentioned measurement electrodes with a barrier element bounding in the direction of the sample, for example an ion-selective membrane or a selective ion-conducting glass. In order also in this case to prevent a diffusion exchange over long periods of time, it is preferred so to compose the lead-off electrolyte that it contains those kinds of ions which are permeable to the barrier element in the same activity as the standard electrolyte. Here, too, it is especially preferred when the lead-off electrolyte has the same composition as the reference electrolyte and the standard electrolyte.

The standard electrolyte can be removed in various ways. In the case of a liquid electrolyte, for example, it can be sucked off or blown off by means of a mouthpiece which can be connected to the hollow chamber or can be dipped into the hollow chamber. Insofar as the hollow chamber is, in toto, readily accessible via its supply opening, it can also be wiped out with an absorbent material, for example a sponge or an absorbent piece of paper.

In order to simplify the handling of the electrode arrangement, in a preferred embodiment the hollow chamber contains a pad impregnated with the standard electrolyte, which pad can be removed after removal of the closure part. After the calibration measurement, the standard electrolyte solution is, together with the pad, removed from the sample chamber.

Since the pad frequently has very small dimensions, it is preferably attached to the closure part. The closure part serves as a means of handling the pad and simplifies the removal thereof from a narrow sample chamber.

The pad is to take up the standard electrolyte completely. Therefore, it preferably consists of an elastic, absorbent material which, prestressed against its elasticity, is enclosed in the hollow chamber. Upon opening the closure part, the pad is decompressed and completely absorbs the standard electrolyte. An especially preferred pad material is a viscose sponge material and particularly a viscose sponge cloth which also contains cotton.

For the accommodation of the pad, there are especially suitable sample chambers constructed as troughs in the base part, the wettable surfaces of the electrodes thereby being provided on the bottom of the trough. In the measurement operational state, the opening of the trough is upward. The wettable surfaces of the electrodes and the bottom of the trough are preferably substantially flat and/or flush with one another in order to simplify the complete removal of the standard electrolyte.

The closure part can be a stopper or lid which can be placed on the trough. In a preferred embodiment, the trough is covered by a flexible foil. Aluminium foils, which are releasably stuck or sealed on to the edge of the trough, can, for example, be used.

Relatively small amounts of liquid are sufficient for the analysis. The electrodes can, therefore, also be accessible on the relatively flat upper side of the base part. In particular, in such embodiments, the pad impregnated with the standard electrolyte can be contained in a trough in the closure part, which again is preferably made from a flexible foil.

As already mentioned above, the reference electrode usually comprises an electron-conducting lead-off contact element and a reference electrolyte, the viscosity of which can also be considerably increased by physicochemical processes like the standard electrolyte. The reference electrolyte is to determine, within the period of time available for the analysis, a predetermined half cell potential, which is as constant as possible, together with the lead-off contact element. Insofar as the standard electrolyte contains ions of a concentration which corresponds to these requirements, the standard electrolyte can, at the same time, be used as the reference electrolyte. In a preferred embodiment of this type, it is provided that at least one of the reference electrodes includes a pad in phase boundary contact with a lead-off contact element, held on the base part, the pad being impregnated with the standard electrolyte of the hollow chamber. In embodiments of this type, no membrane is necessary between the reference electrolyte and the standard electrolyte or during the analytical measurement between the reference electrolyte and the liquid sample to be analysed. The pad can be, for example, a piece of paper impregnated with the standard electrolyte lying against the lead-off contact element. Whereas, before the analytical measurement, the standard electrolyte is removed from the region of the ion-selective measurement electrode, the pad impregnated with the electrolyte remains on the base part. The standard/reference electrolyte can be thickened in the region of the reference electrode for the formation of the pad. The liquid to be analysed wettens during the analytical measurement not only the pad impregnated with the standard electrolyte or the gel layer of the thickened electrolyte but also the ion-selective measurement electrode. The standard/reference electrolyte can, as explained above, be contained in a removable pad which, in the hollow chamber, lies against the pad of the reference electrode.

In another preferred embodiment, the base part carries a pump means connected with the hollow chamber or a mouthpiece closed with a removable closure part for connection to a pumping device. In this embodiment, too, the electrodes are preconditioned by the liquid standard electrolyte introduced into the hollow chamber by the manufacturer. Before the actual analytical measurement, a calibration measurement can be carried out, after which the standard electrolyte is blown out of the sample chamber by means of the pumping device but is preferably sucked out. The pumping device can be a folded bellows held on the base part and, together with this, forming a disposable unit, the inner chamber of the folded bellows being connected with the hollow chamber. Alternatively, a cylindrical opening can be provided in the base part, which cylindrical opening is closed, on the operational side, by a piston slidable therein.

The pumping device is preferably used not only for the removal of the standard electrolyte but also for supplying the sample chamber formed by the hollow chamber with the liquid to be analysed. For this purpose, the base part preferably has the shape of a pipe, the end opening of which forming the supply opening is closed by means of a closure part and the other end carries the pumping device or is also closed by means of a closure part.

The measurement electrode or electrodes, on the one hand, and the reference electrode, on the other hand, can be arranged side-by-side in the axial direction of the pipe, the measurement electrode preferably being arranged between the supply opening and the reference electrode. This construction is especially advantageous when the standard electrolyte at the same time forms the reference electrolyte of the reference electrode. In this case, the standard electrolyte does not have to be completely sucked out of the pipe but rather it suffices when, before sucking in the liquid to be analysed, a small air bubble is sucked in. Between the measurement electrode and the reference electrode, the capillary electrolyte layers remaining on the inner surface of the pipe in the region of the air bubble form an electrolyte bridge which conductively joins together the two electrolytes. The electrolyte bridge prevents the mixing of the standard electrolyte with the liquid to be analysed.

According to a second main aspect of the present invention, which is independent of the first one, this is directed towards an electrode arrangement with a reference electrode which is simple and economic to produce and, at the same time, has an outstanding stability and short adjustment time.

This is characterised, in the case of an electrode arrangement of the initially described kind, in that the reference electrode has a lead-off contact element with elementary copper and the reference electrolyte contains a copper salt and, without a salt bridge being inserted therebetween, is adapted to be brought into phase boundary contact with the sample. A high concentration of copper salt is preferably used.

Although numerous reference electrode systems have previously been described, in practice, in conjunction with ion-selective electrodes, there have been practically exclusively used reference electrodes based on silver-silver chloride or calomel reference electrodes. The silver-silver chloride reference electrode is thereby characterised in that, in its case, as reference electrolyte it is possible advantageously to use potassium chloride. The potassium and chloride ions form a so-called equitransferant ion pair, diffusion potentials on the phase boundary to the sample or to the standard being, in the case of the measurement, practically completely avoided. This has been known for a long time and is a frequently used property of potassium chloride. Insofar as other reference electrodes are used, these are normally connected with the sample via a so-called salt bridge which consists of a concentrated potassium chloride solution. In this way, the advantageous properties of potassium chloride are also utilised for reference electrode systems which make use of another reference electrolyte. However, this construction has the disadvantage that a system of at least three chambers must be used, namely, connected successively to one another, a chamber for the reference electrolyte of the reference electrode, a chamber for the salt bridge and a sample chamber with the measurement electrode arranged thereon, which is possibly followed by yet a further chamber for the conducting-off electrolyte of the measurement electrode. This construction can be considerably simplified when the salt bridge can be omitted, which is of considerable importance for an electrode arrangement which can only be used once.

Surprisingly, we have now found that a reference electrode without salt bridge, at least for the determination of components of body fluids and especially of blood, can be constructed in a very simple manner when there is used a system of copper and a copper salt and especially of copper-copper sulphate. Practical experiments have shown that, with this system, outstandingly stable reference electrodes can be constructed which, at the same time, are characterised by very short adjustment times. Although, in the case of copper and sulphate, the ions are not an equitransferent ion pair, surprisingly, no disturbing diffusion potential differences could be ascertained with regard to blood. This is all the more surprising since the reference electrode system according to the present invention operates with a relatively high concentration of copper salt, preferably of the order of 1 mol/litre. In comparison with potassium chloride, the copper-copper salt system has the additional advantage that, in contradistinction to potassium chloride, it does not negatively influence the blood measurement material.

The reference electrolyte containing the copper salt can be brought into a state of high viscosity by suitable processes, for example as a thickened gel. Insofar as a liquid salt solution is used as reference electrolyte, which has proved to be useful in practice, it is preferable, in the region of the point of contact to the sample, to provide an electrolyte bridge which, on the one hand, restrains mixing up of sample and reference electrolyte and, on the other hand, must be permeable to all kinds of ions. In practice, it has proved to be especially useful to use a cellulose acetate membrane with a pore size of about 1 $\mu$m. By means of the constructional part forming the electrolyte bridge, especially the membrane, a closed-off electrolyte chamber of the reference electrode is bounded, which is filled with the liquid reference electrolyte. Depending upon the desired maximum measurement time, it is now of importance so to construct this sample chamber that the sample brought into contact with the electrolyte bridge cannot influence the stable half cell potential of the reference electrode within the desired measurement time. According to a preferred embodiment, this is achieved in that the electrode chamber has a sufficient great distance between electrolyte bridge and lead-off contact element and/or has a sufficiently small cross-section on this path so that, in the desired measurement time, no ions from the sample can get as far as the lead-off contact element and thereby impair the reference potential.

For the construction of the electrode arrangement as a disposal electrode for single use, which is desired according to the present invention, a simple and economic production is of especial importance. For this purpose, it has proved to be especially useful to as lead-off contact element instead of, for example, a copper wire, a graphite-copper mixture bound with a binding agent. An alternative construction, which is also easy to produce, provides that the lead-off contact element consists essentially of a graphite strip and especially one produced by a printing process on the insulation body, on which strip is coated with copper, also by a printing process, in the region in contact with the reference electrolyte.

The application of the copper-graphite mixture or of the pure graphite strip on to the insulating body takes place according to a printing process, known for other purposes, in the following manner: a metal plate is etched with the appropriate conductive strips to a depth of about 20 to 40 $\mu$m. The layer of copper-graphite lacquer or of pure graphite lacquer there applied with a so-called "dye rake" is removed with the help of a flexible silicone stamp and transferred to the insulating body. Such a process can be used with short rhythmic periods in a process suitable for large-scale production.

The same process is preferably also used for the production of the lead-off contact elements of the at least one measurement electrode in order to be able to produce the whole electrode arrangement with the fewest possible working steps.

The present invention will now be described in more detail, with reference to the accompanying drawings, in which.

Figures 1, 2:
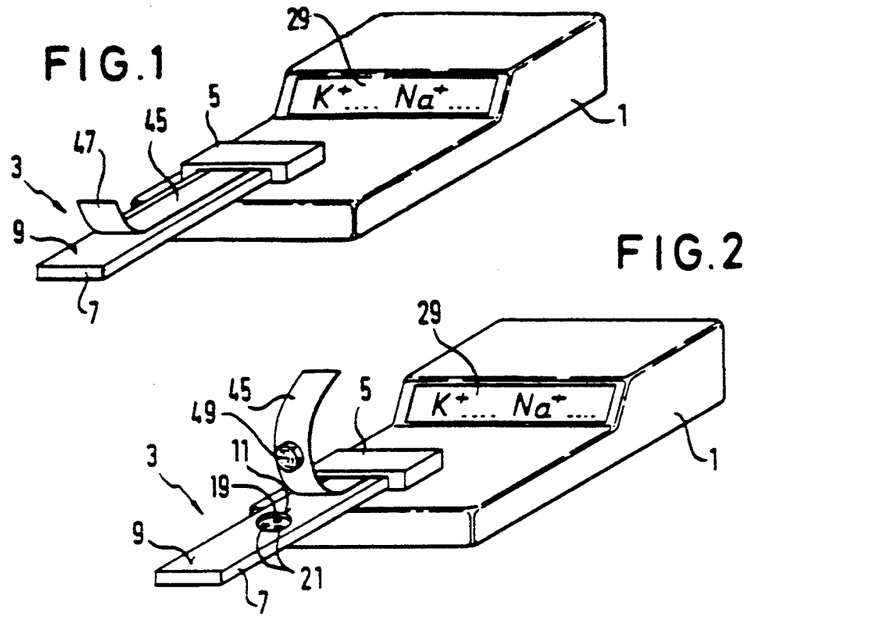
FIG. 1 is a perspective view of an analysis apparatus for the determination of sodium and/or potassium ion concentrations in a body fluid, especially in blood, in the case of carrying out a calibration measurement.
FIG. 2 is a perspective view of the apparatus according to FIG. 1 in the case of carrying out an analytical measurement.
Figure 3:
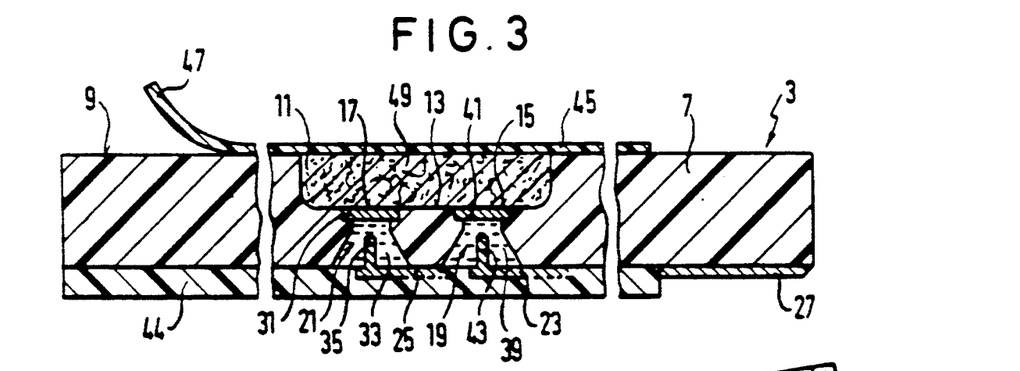
FIG. 3 is a schematic longitudinal section through an electrode unit usable in the apparatus according to FIG. 1 in the state produced by the manufacturer and prepared for the calibration measurement.
Figure 4:
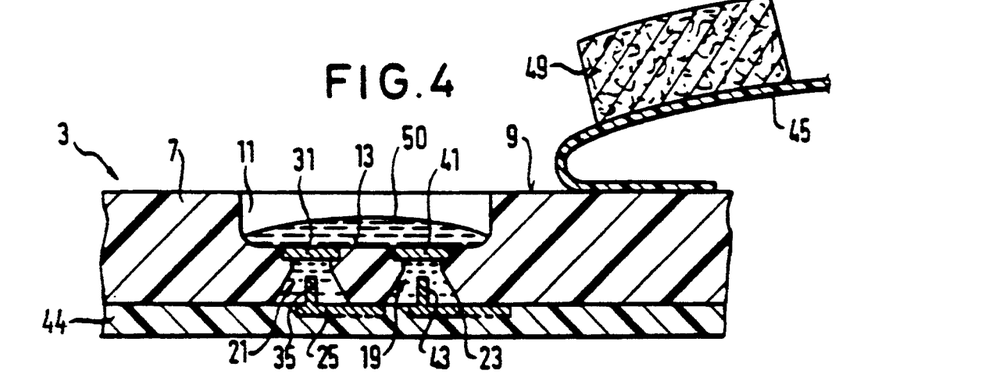
FIG. 4 is the electrode unit according to FIG. 3 but which has been prepared for the analytical measurement.

FIGS. 1 and 2 show an analysis apparatus 1 which can be used, for example, for the measurement of the concentrations of sodium and/or potassium ions in blood or urine. The measurement takes place with the help of an electrode unit 3, constructed as a disposable part, which is electrically and mechanically connected with the analysis apparatus 1 via an electrical insert connection 5. As is best shown in FIGS. 3 and 4, the electrode unit 3 has a strip base part 7 made of an insulating material, for example a synthetic resin, which, on the upper part of its operational flat side 9, inserted into the insert connection 9, has a trough 11 with a preferably flat bottom 13. Wetting surfaces 15 and 17 of a reference electrode 19 and of two ion-selective measurement electrodes 21 are flush with the bottom 13. The reference electrode 19 and the measurement electrodes 21 are spaced apart. For the sake of clarity, FIGS. 3 and 4 only show one of the measurement electrodes 21. One of the measurement electrodes 21 is potassium selective and the other is sodium selective. In the case of an appropriate construction of the measurement electrodes, concentrations of other kinds of ions can also be measured. The reference electrode 19 and the measurement electrodes 21 are galvanically connected via electric leads 23, 25 with insert contacts indicated at 27. The insert contact 27 produces, via the insert connection, the electrical connection to a high ohmic voltage measurement device to be connected between the reference electrode 19, on the one hand, and the measurement electrodes 21, on the other hand, the voltage values of the voltage measurement device being shown on an indicator panel 29 (see FIGS. 1 and 2), after recalculation, as sodium or potassium ion concentrations.

Each of the two measurement electrodes 21 includes, in the illustrated embodiment, a membrane 31, selective for sodium or potassium ions, forming the wetting surface 17, which membrane closes the trough 11 opposite an electrolyte chamber 33 filled with a conducting-off electrolyte. The conducting-off electrolyte can be a gel containing potassium chloride, sodium chloride or silver chloride. A lead-off contact element 35, connected with a lead 25, dips into the lead-off electrolyte. The lead-off contact element can be a silver wire with a silver chloride surface layer which, together with the lead-off electrolyte, forms a silver/silver chloride electrolyte system. The lead-off electrolyte is saturated with silver chloride and also contains the kind of ion for which the membrane 31 is selective.

The reference electrode 19 has an electrolyte chamber 39 which contains a gel containing potassium chloride, sodium chloride or silver chloride as reference electrolyte. A membrane 41 forming the wetting surface 15 and permeable to all kinds of ions closes off the electrolyte chamber 39 in the direction of the trough 11. A lead-off contact element 43 connected to a lead 23 dips into the electrolyte chamber 39, the lead-off contact element 43 reacting reversibly electrochemically with the reference electrolyte. The lead-off contact element 43 is again a silver wire with a silver chloride surface layer. The electrolyte chambers 33 and 39 are closed by a layer 44 which is impermeable to water vapour.

In the state illustrated in FIG. 3 of the electrode unit 3, as supplied by the manufacturer, the opening of the trough 11 is closed by a foil strip 45, which is applied to the surface 9 of the base part 7, for example is stuck thereon, the foil strip 45 ending in a grippable lug 47 which simplifies the pulling off of the foil 45. In the trough 11, there is provided a pad 49 of a material which, at least in a moist state, is elastic and absorbent, for example of fleece, which pad 49 has been impregnated by the manufacturer with a standard electrolyte solution. Furthermore, the material should be hydrophilic and swellable and readily connectible with the material of the foil strip, especially by heat-sealing. It must, of course, in no way impair the standard electrolyte solution or the electrode function. Particularly suitable is a viscose sponge material, especially a cotton-viscose sponge cloth (cf. Vieweg/Becker, Kunststoffhandbuch, Vol. III, "Abewandelte Naturstoffe", pub. Carl Hahset Verlag, Munchen, 1965, pages 150–158). The dimensions of the pad 49 correspond approximately to the dimensions of the trough 11. The thickness of the pad 49 is such that, when introduced into the trough 11, it is compressed and lies elastically, springingly tensioned against the wetting surfaces 15, 17 of the electrodes 19, 21. The standard electrolyte solution contains sodium and potassium ions in a predetermined concentration and provides for a constant preconditioning of these electrodes.

For an analytical measurement of the sodium and potassium concentrations, the electrode unit 3 provided with standard solution by the manufacturer is, as illustrated in FIG. 1, inserted, without removal of the foil strip 45, into the insert connection 5 of the analysis apparatus 1. The analysis apparatus 1 measures the sodium and potassium ion concentrations of the standard solution and is hereby automatically calibrated. The foil strip 45 is then pulled off. The pad 49 fixed on to the foil strip 45 expands and completely sucks up from the bottom 13 of the trough 11 any possible residues of the standard electrolyte solution. Into the now exposed trough 11 there is dropped in a sample, indicated by 50, of, for example, 50 $\mu$l. of blood to be analysed. The analysis apparatus 1 measures the sodium and potassium ion concentration and indicates the measurement values, which have been calculated with the use of the previously determined standard values, on the indicator panel 29.

Figure 5:
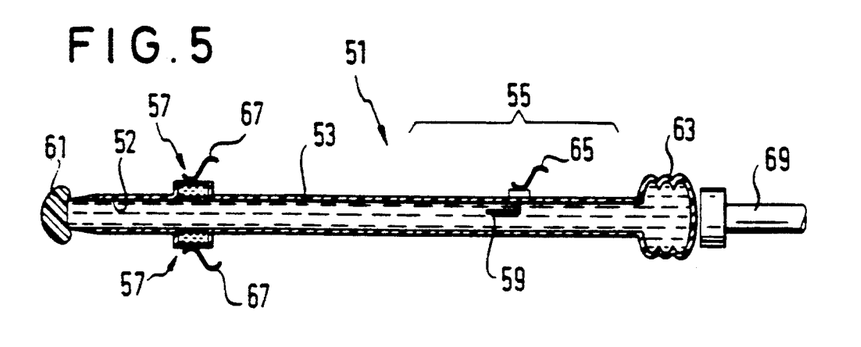
FIG. 5 is another embodiment of an electrode unit produced by the manufacturer and prepared for a calibration measurement, for use in an analysis apparatus for the determination of electrolytic components of a liquid, especially blood or urine.
Figure 6:
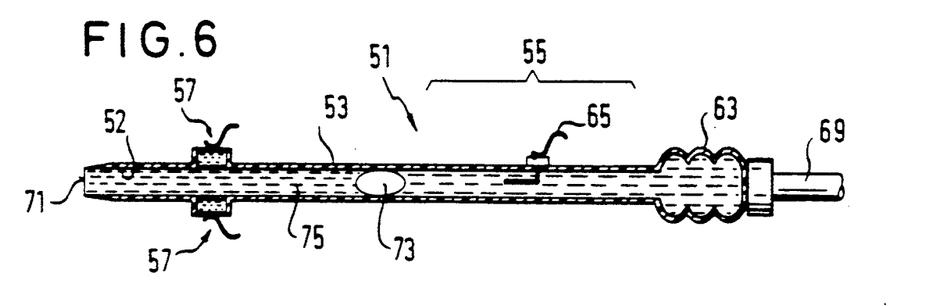
FIG. 6 is a schematic illustration of the electrode unit according to FIG. 5 during the analytical measurement.

FIGS. 5 and 6 show another embodiment of an electrode unit 51 for an analysis apparatus of the kind illustrated in FIGS. 1 and 2. The electrode unit 51 is again a disposable part which permits a single analytical measurement. The electrode unit 51 includes an insulating tube 53, consisting, for example, of glass but preferably of synthetic resin, forming a hollow chamber 52, which insulating tube 53 carries a reference electrode 55 and, in the axial direction of the insulating tube 53, two ion-selective measurement electrodes 57 which, in the illustrated embodiment, lie diametrically opposite one another. The ion-selective measurement electrodes 57 react selectively to different kinds of ions, for example sodium or potassium ions. The measurement electrodes 57 can be constructed corresponding to the measurement electrodes 21 described above with reference to FIGS. 1 to 4. The reference electrode 55 can be constructed corresponding to reference electrode 19, in which case, in order to save sample volume, it can also be arranged opposite the measurement electrodes 57 in the region of the opening 71 of the tube 53. In the illustrated embodiment, the reference electrode 55 does not include a separate reference electrolyte chamber but merely, a lead-off contact element 59, which projects into the inner chamber of the insulating tube 53. The insulating tube 53 is closed, on the end side adjacent the measurement electrodes 57, by a removable cap 61 and, on its opposite end, carries an elastic bellows 63 extending in the direction of expansion. The bellows 63 and the insulating tube 53 are filled with an electrolyte solution which contains the kinds of ions to be analysed, for example sodium or potassium ions, in constant concentration. The electrolyte solution introduced into the insulating tube 53 by the manufacturer wettens not only the lead-off contact element 59 of the reference electrode but also the ion-selective measurement electrodes 57 and serves not only as standard electrolyte solution for a calibration measurement but also as lead-off electrolyte of the reference electrode 55.

FIG. 5 shows the electrode unit 51 inserted into the analysis apparatus, which is not shown in detail. The analysis apparatus carries spring connection contacts 65 and 67 which, when the electrode unit 51 is placed in the analysis apparatus, produce the electrical connection between the electrodes and a high ohmic voltage measurement device of the analysis apparatus. The analysis apparatus also includes a manually or motor-driven slidable operating plunger 69, with the help of which the volume of the bellows 63 can be controlled. FIG. 5 shows the operating plunger 69 in a calibration position in which the bellows 63 is compressed to such an extent that the standard/reference electrolyte solution introduced by the manufacturer wettens not only the lead-off element 59 of the reference electrode but also both measurement electrodes 57. In this position, the operating plunger 69 must not lie against the bellows 63 since this, because of the cap 61 still being in position, is held in the illustrated contracted state. The analysis apparatus is calibrated by means of the standard/reference electrolyte solution introduced by the manufacturer.

For the analytical measurement of, for example, blood or urine, the cap 61 is removed from the supply opening marked 71 of the insulating tube 53 and, by pulling back the operating plunger 69, an air bubble 73 is first sucked in and then a sample of the liquid to be analysed, indicated by 75 in FIG. 6. The air bubble 73 is sucked in between the reference electrode 55 and the measurement electrodes 57 and, in the region of the inner wall of the tube, forms a capillary electrolyte bridge between the reference electrolytes in the region of the reference electrode 55 and the liquid to be analysed. The electrolyte bridge of the air bubble 73 separates the region of the standard/reference electrolyte solution of the reference electrode from the region of the liquid to be analysed.

Figure 7:
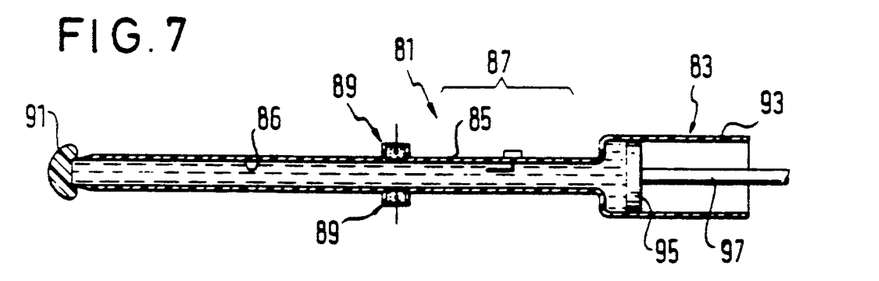
FIGS. 7 and 8 are illustrations of other embodiments of electrode units for the determination of electrolytic components of liquids, especially blood and urine.

FIG. 7 shows another embodiment of an electrode unit 81 in the form supplied by the manufacturer which differs from the electrode unit 51 of FIGS. 5 and 6 only in that, instead of the bellows 63, there is provided a piston-cylinder unit 83 for sucking in an air bubble and the liquid to be analysed, for example blood or urine. The electrode unit 81 again includes an insulating tube 85 with a reference electrode 87, as well as two ion-selective measurement electrodes which are spaced apart from one another and from the reference electrode 87. The insulating tube 85 forms a hollow chamber 86 and, on the end remote from the piston-cylinder unit 83, is closed by the manufacturer by a cap 91 and contains a standard-reference electrolyte solution introduced by the manufacturer. The piston-cylinder unit 83 includes a cylinder 93, preferably formed by a cross-sectional enlargement of the tube 85, as well as a tight-fitting piston 95 slidable in the cylinder. The piston rod 97 of the piston 95 can be coupled with an operating mechanism of an analysis apparatus in a manner which is not illustrated in detail.

The reference electrode 87, as well as the measurement electrodes 89, are constructed in a manner appropriate for the electrode unit 51. In both embodiments, the reference electrode 55 or 87 can be separated from the standard electrolyte solution by an electrolyte bridge. In these embodiments, the bellows 63 or the piston-cylinder unit 83 sucks in standard solution in the direction of the reference electrode so that the liquid to be analysed also wettens the measurement electrodes and the standard solution wettens the lead-off contact element of the reference electrode.

Figure 8:
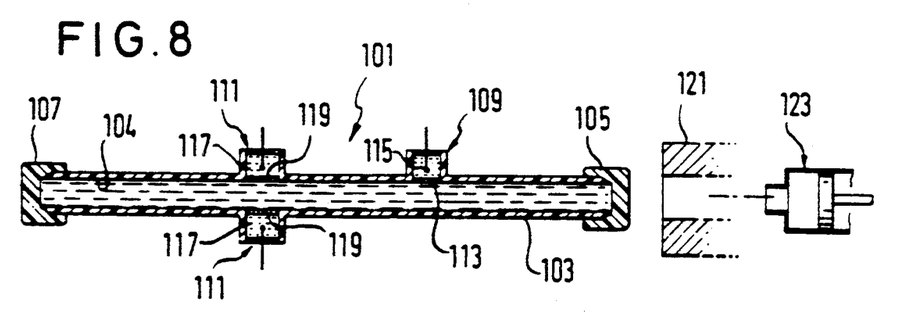

An embodiment of the last-mentioned kind is illustrated in FIG. 8, which shows an electrode unit 101 with an insulating tube 103, the ends of which are tightly closed by removable caps 105, 107. The insulating tube 103 forms a hollow chamber 104 and carries, axially displaced from one another, a reference electrode 109, as well as two diametrically opposed ion-selective measurement electrodes 111. The reference electrode 109 and the measurement electrodes 111 are constructed correspondingly to the electrodes 19 and 21 of electrode unit 3 of FIGS. 1 to 4. A membrane 113 separates the inner chamber of the tube 103 from an electrolyte chamber 115, filled with a reference electrolyte, of the reference electrode 109. Such a reference electrode 109 can advantageously also be arranged at another position of the tube 103. An especially small mode of construction can be achieved when it is positioned opposite the measurement electrodes 111 in the region of the tube opening at 107.

Electrolyte chambers 117, filled with lead-off electrolyte, of the measurement electrodes 111 are separated by ion-selective membranes 119 from the inner chamber of the insulating tube 103. The inner chamber is filled by the manufacturer with a standard electrolyte solution which contains the kind of ions to be analysed in a constant, predetermined concentration and constantly wettens the membranes 113, 119 and thus preconditions.

After removal of the cap 105, the tube 103 can be connected to a mouthpiece 121 of a schematically illustrated suction pump 123 or the like of an analysis apparatus which is not illustrated in detail. The cap 105 can possibly be punctured by a canula or a barb-shaped piston so that it does not have to be removed. Connection contacts of the analysis apparatus, which are not illustrated in detail, connect the reference electrode 109 and the measurement electrodes 111 with a high ohmic voltage measurement device. The analysis apparatus is calibrated by the standard electrolyte solution which has been introduced by the manufacturer.

For the analytical measurement of, for example blood or urine, the cap 107 is removed and the standard electrolyte solution sucked off by means of the suction pump 123 at least to over the reference electrode 109. The liquid to be analysed is then sucked in until it wettens the reference electrode 109 and the two measurement electrodes 111 and the analysis measurement is carried out.

Instead of the reference electrode 109, there can also be used a reference electrode similar to the electrode 55 of FIGS. 5 and 6 when the manufacturer has introduced a standard/reference electrolyte solution and, before sucking in the liquid to be analysed, an air bubble is sucked in between the reference electrode and the measurement electrodes for the formation of an electrolyte bridge. The liquid to be analysed is then sucked in up to the lead-off contact element of the reference electrode.

Figure 9:
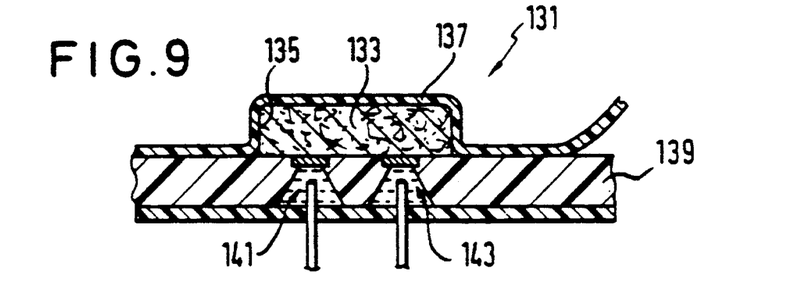
FIGS. 9 to 16 illustrate further embodiments of electrode units produced by the manufacturer and prepared for a calibration measurement, for the determination of electrolytic components of liquids, especially of blood or urine, FIGS. 9, 11, 13 and 15 illustrating the electrode units in the state produced by the manufacturer and prepared for the calibration measurement and FIGS. 10, 12, 14 and 16 illustrating the electrode units during the analytical measurement.
Figure 10:
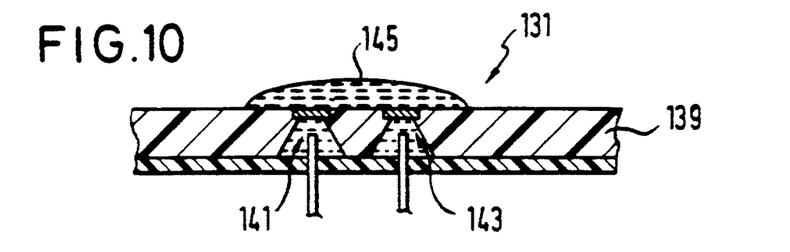

FIG. 9 shows another embodiment of an electrode unit 131 which essentially only differs from the electrode unit 3 of FIG. 3 in that its pad 133 impregnated with standard solution is housed in a trough 135 of a foil strip 137. The foil strip 137 is removably applied to an insulating base part 139 which, in turn, carries a reference electrode 141 and at least one ion-selective measurement electrode 143. The elements 133 to 143 of the electrode unit 131 correspond consecutively to the elements 49, 11, 45, 7, 19 and 21 of the electrode unit 3 of FIG. 3. For the explanation of its construction, of the manner of operating and of its use, reference is made to the description of FIGS. 1 to 4. However, in contra-distinction to the electrode unit 3, the upper-lying side of the base part 139 in the position of use is flat. For the analytical measurement, as shown in FIG. 10, a drop 145 of blood to be analysed is dropped on to the flat upper side of the base part 139 so that it jointly covers the upper-lying uncovered wetting surfaces of the electrodes 141 and 143.

Figure 11:
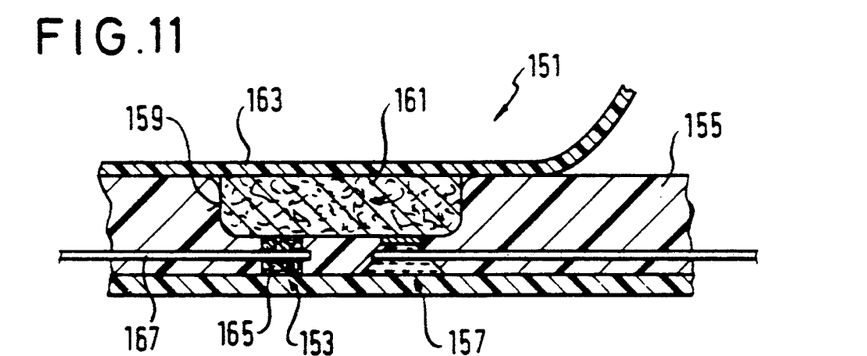
Figure 12:
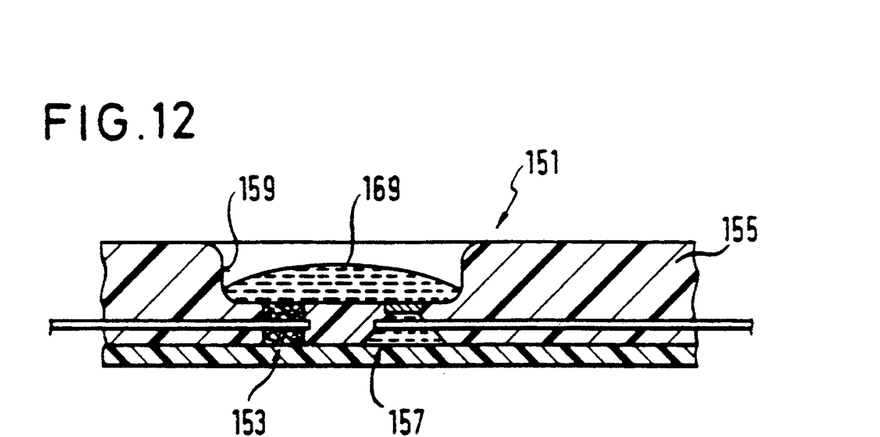

FIGS. 11 and 12 show an electrode unit 151 which essentially differs from the electrode unit 3 of FIGS. 3 and 4 only by the construction of its reference electrode 153. The electrode unit 151 again has an insulating base part 155 which, besides the reference electrode 153, carries at least one ion-selective measurement electrode 157. The electrodes 153, 157 are provided on the bottom of a trough in the base body, which trough, in the operating position, is open at the top. As is to be seen from FIG. 11, the trough contains a pad 161 which is applied to a foil strip 163 covering and tightly sealing the trough 159. The pad 161 is again impregnated with a standard electrolyte solution by the manufacturer. The composition of the standard electrolyte is so chosen that the standard electrolyte simultaneously constitutes the reference electrolyte of the reference electrode 153. The reference electrode 153 includes a body 165 impregnated with standard/reference electrolytes, this body 165 lying against the pad 161. The impregnated body 165 can be, for example, a piece of fleece or sponge or a piece of paper. Porous solid bodies or a highly thickened gel can, however, also be used. The standard/reference electrolyte in the body 165 is in phase boundary contact with an electron-conducting lead-off contact element 167.

FIG. 11 shows the electrode unit 151 in the form produced by the manufacturer in which the calibration measurement is also carried out. FIG. 12 shows the electrode unit 151 with the foil strip 163 removed. A drop 169 of the liquid to be analysed is introduced into the trough 159, this liquid being, for the analytical measurement, in phase boundary contact with the standard-/reference electrolytes in the body 165 of the reference electrode 153, as well as being in phase boundary contact with the measurement electrodes 157. For the further explanation of the details of construction and of the method of use of the electrode unit 151, reference is made to the description of FIGS. 1 to 4, the parts 155 to 163 corresponding consecutively to parts 7, 21, 11, 49 and 45.

Figure 13:
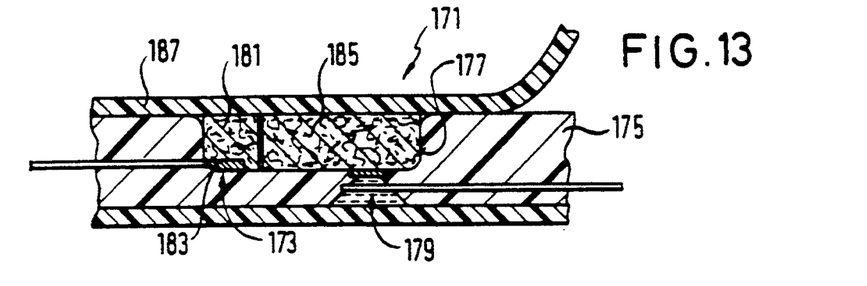
Figure 14:
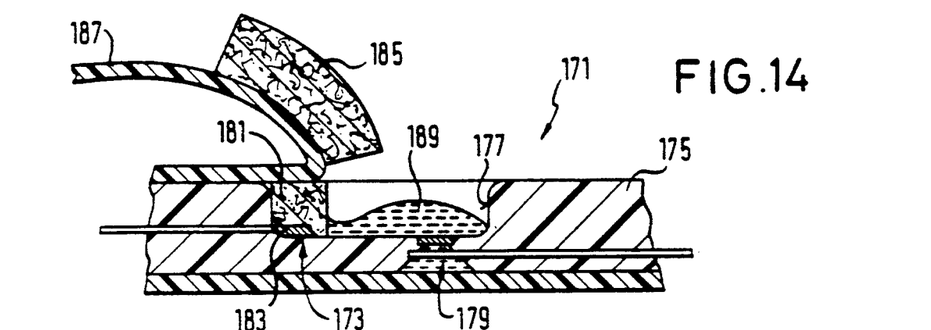

FIGS. 13 and 14 show an electrode unit 171 which essentially differs from the electrode unit 151 of FIGS. 11 and 12 only in that its reference electrode 173 is not housed in a separate chamber of an insulating base part 175 but rather in a trough 177 which, in the operational position of the electrode unit, is upwardly open in such a manner that its phase boundary surface to the standard/reference electrolyte or to the liquid to be analysed forms one of the upright walls of the trough 177. The reference electrode 173 includes a pad 181 fixed in the trough 177 and impregnated with the standard/reference electrolyte, this pad 181 being in phase boundary contact with a lead-off contact element 183. Furthermore, the trough contains another pad 185 impregnated with the standard/reference electrolyte, this pad 185 lying flatly not only against the pad 181 but also against the wetting surface of the measurement electrode 179. The pad 185 is fixed to a foil strip 187 which closes the trough 177 and is removably applied to the base part 175. The pads 181 and 185 can merely be in contact with one another but they can also be connected together in one piece by a separating member, which is not illustrated in detail, in such a manner that the separating member is torn off upon pulling off the foil strip 187. FIG. 13 shows the electrode unit 171 in the state in which it is provided by the manufacturer. FIG. 14 illustrates the electrode unit 171 during the analytical measurement, a drop 189 of the liquid to be analysed being introduced into the trough 177. Parts 173 to 187 correspond consecutively to parts 153, 155, 159, 157, 165, 167, 161 and 163 of electrode unit 151 of FIGS. 11 and 12. For the further explanation of the construction and of the method of use, reference is made to the description of these Figures, as well as to the description of FIGS. 1 to 4.

Figure 15:
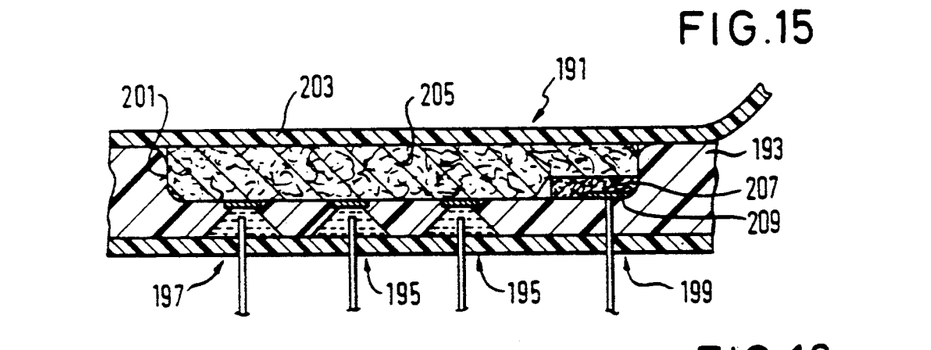
Figure 16:
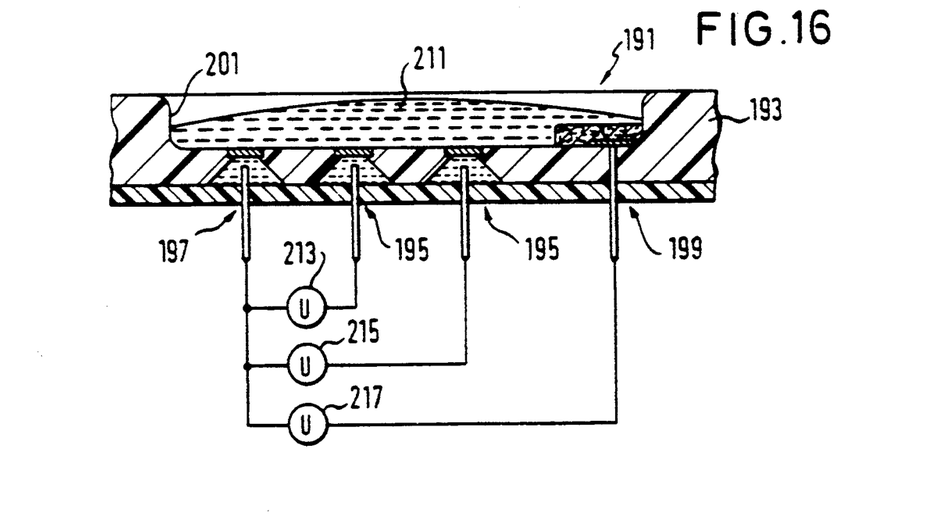

FIGS. 15 and 16 show an electrode unit 191 which essentially differs from unit 3 of FIGS. 3 and 4 only in that on to a base body 193 there are applied not only several ion-selective measurement electrodes 195 but also two reference electrodes 197 and 199. The electrodes 195, 197 and 199 are again wettable in a trough 201 of the base part 193, which trough is upwardly open in the operational position of the electrode unit 191. For the achievement of a capillary action, the trough 201 has a longitudinally extended shape and is tightly closed by a removable foil strip 203 fixed on to the base part 193. In the trough 201, there sits a prestressed pad 205 which is fixed to the foil strip 203 and is removable together with the foil strip 203, this pad 205 lying against all the electrodes 195, 197 and 199. The pad 205 is impregnated by the manufacturer with a standard-/reference electrolyte which preconditions the electrodes and makes possible a calibration measurement.

The ion-selective measurement electrodes 195 and the reference electrode 197 have the construction described for electrodes 19 and 21 in FIGS. 3 and 4. The reference electrode 199 is constructed similarly to reference electrode 153 in FIG. 11 or to reference electrode 173 in FIG. 13 and has a body 207 impregnated with the standard/reference electrolyte, said body 207 being, for example, a piece of paper fixed to the bottom of the trough 201, which piece of paper is in phase boundary contact with a lead-off contact element 209.

With the foil strip 203 and the pad 205 removed, for the analysis measurement a drop 211 of the liquid to be analysed is introduced into the trough 201 in such a manner that all the electrodes are wetted. FIG. 16 shows schematically a voltage measurement device 213 connected between the reference electrode 197 and one of the ion-selective measurement electrodes. Between the other measurement electrode 195, selective for another kind of ion, and the reference electrode 197, there is connected another voltage measurement device 215. The voltage measurement devices 213, 215, which can be formed by a common but switchable measuring device, measure the potential differences between the electrodes 195 and 197. Between the reference electrodes 199 and 197 is connected a further voltage measurement device 217, the potential difference measured by this voltage measurement device providing a control value for the correction of the measurement values of the voltage measurement devices 213, 215.

The reference electrode 199 can be constructed correspondingly to the reference electrode 197 with the use of a porous membrane which is ion non-specific. Alternatively, the reference electrode 197 can be constructed analogously to the reference electrode 199. The reference electrodes 197, 199 are preferably arranged on opposite sides of the ion-selective electrodes 195.

Figure 17:
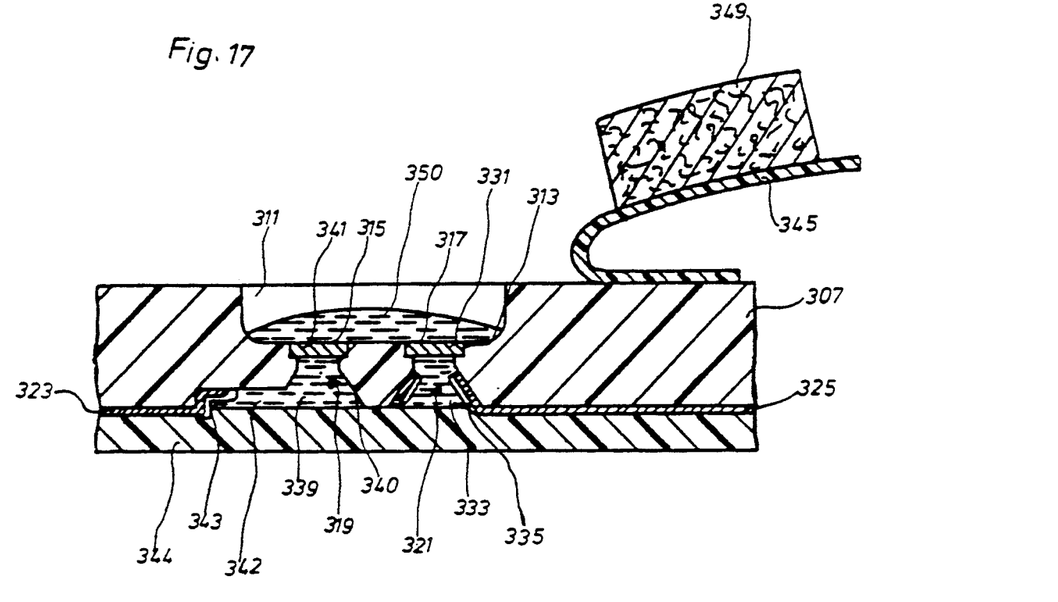
FIG. 17 illustrates an electrode unit, using the second main aspect of the present invention, in schematic longitudinal section during an analytical measurement.

FIG. 17 shows an electrode unit during the analytical measurement in which the second main aspect of the present invention is put into practice, by way of example. The illustration corresponds essentially to FIG. 4, reference thus being made to the description of FIG. 4. The corresponding constructional parts are indicated by reference numerals which are increased in value by 300 in comparison with those in FIG. 4. At this point, only those special features are described in detail in which the embodiment illustrated in FIG. 17 differs from that illustrated in FIG. 4.

This is, in the first place, the composition of the reference electrolyte present in the electrode chamber 339 and the construction of the lead-off contact element. As reference electrolyte, there is used a copper salt solution which practically completely fills the electrode chamber 339, which is closed by a membrane 341 permeable to all kinds of ions. The electric lead 323 is formed by a strip of graphite which has been printed on to the base body 307 by the process described hereinbefore. The lead-off contact element is formed by a copper layer 343 which covers the graphite strip in such a manner that the reference electrolyte is only in contact with the copper.

Furthermore, it can be seen that the electrode chamber 339 is divided into a region 340, which widens downwardly in the form of a truncated cone, and into a narrow canal 342. The narrow canal has such a great length (in FIG. 17, in the plane of the drawing, from right to left) and such a small cross-section that, in the measurement operational state illustrated in the Figure, within the desired measurement time, no ions from the sample can penetrate into the region of the lead-off contact element 343 and thereby endanger the stability of the reference potential.

In the illustrated preferred embodiment, the electric lead 325 and the lead-off contact element 335 of the measurement electrode 321 is also constructed analogously to the reference electrode 319. If this construction is used together with a copper salt solution present in the electrolyte chamber 333 of the measurement electrode 321, then in toto, there is provided an electrode arrangement which can be produced with only a few working steps because the materials used in both electrodes are the same. Both electrodes are in contact with the standard electrolyte used for the impregnation of the pad 349 which contains the same copper salt in the same concentration. Thus a system is formed in which, even over long storage periods, a state of equilibrium is maintained in the whole of the measurement arrangement. When this electrode arrangement is connected to the measurement apparatus, a standard potential is immediately obtained. After tearing off the foil strip 345 and thus removing the pad 349 containing the standard electrolyte, the blood sample 350 can be applied. The system is then very quickly adjusted to a stable value, especially in the case of using the electrolytes containing a copper salt in the reference electrode 319 and in the measurement electrode 321, which stable value can be measured and used for the desired analysis.

The ion-selective measurement electrodes explained in the above embodiments of the electrode units are preferably constructed with the use of an ion-selective membrane. A suitable potassium ion-selective membrane includes, according to a generally known formulation, the following amounts, expressed in percentages by weight:

0.1 to 3%, preferably 1%, valinomycin
20 to 50%, preferably 33%, polyvinyl chloride
50 to 80%, preferably 66%, sebacic acid bis-(2-ethylhexyl ester); $C_{26}H_{50}O_4$ Suitable sodium ion-selective membranes are described, for example, in the dissertation of H. F. Osswald "Beitrag zur Entwicklung ionenselektiver Durchfluss-Flussigkeitmembranelektroden für die Bestimmung von Natrium-, Kalium, Calcium- and Chlorid-Ionen in Vollblut", Diss. ETH 6480, 1979 Eidgenössische Technische Hochschule, Zurich, and in Medical and Biological Application of Electrochemical Devices, edited by Jiri Koryta, P. C. Meier et al., pages 13 to 91. A suitable composition for this purpose is the following, expressed in percentages by weight:

0.5 to 10%, preferably 5%, Ligand ETH 227
50 to 80%, preferably 63.2%, sebacic acid bis-(2-ethylhexyl ester); $C_{26}H_{50}O_4$
20 to 50%, preferably 31.8%, polyvinyl chloride.

For the lead-off electrolyte in the case of the determination of potassium ions, there can, for example, be used the following composition:

1 to 1000 mmol/litre copper sulphate + 10 mmol/litre potassium chloride in contact with copper wire; or
5 to 100 mmol/litre sodium chloride (water) + 10 mmol/litre potassium chloride (saturated with silver chloride) in contact with silver/silver chloride wire.

As standard solution, there can be used a solution with 5 mmol/litre potassium chloride or 145 mmol/litre sodium chloride.

For the reduction of the diffusion potential, 1 to 3 mol/litre potassium chloride is preferably added to the reference electrolyte when the reference electrolyte and the standard electrolyte are different. If the reference electrolyte and the standard electrolyte are identical, then the ion concentration can be increased by the addition of copper sulphate and/or magnesium chloride end/or lithium acetate. The potassium and sodium ion-selective membranes must then be so chosen that they do not correspond to these ions or correspond to them in a predeterminable way. The above-described potassium ion-selective membranes are insensitive, for example, to copper ions.

In the case of the electrode units 151, 171 and 191 of FIGS. 11 to 16, the pad impregnated with the standard electrolyte sits in a trough in the base part. Corresponding to the electrode unit 131 of FIGS. 9 and 10, it can, alternatively, also be housed in a trough in the closure part.

It will be understood that the specification and examples are illustrative but not limitative of the present invention and that other embodiments within the spirit and scope of the invention will suggest themselves to those skilled in the art.

We claim:

1. A method for the electrochemical analysis of a species of ions in a sample liquid comprising providing an electrode arrangement having
   a base body made of an insulating material and
   a removable closure part which, together with the base body, forms a closed hollow chamber,
   a measurement electrode and a reference electrode held on the base body,
   said measurement electrode and said reference electrode having wettable surfaces towards said closed hollow chamber,
   said reference electrode comprising an electron-conducting lead-off contact element and a reference electrolyte containing a species of ions which makes a reversible electrochemical reaction with the lead-off contact element to provide a reference potential independent of the liquid to be analyzed, said closed hollow chamber containing a liquid preconditioning electrolyte prepacked by the manufacturer in phase boundary contact with said measurement electrode and said reference electrode and containing the species of ions to be analyzed and the species of ions which makes a reversible electrochemical reaction with the lead-off contact element of the reference electrode, said phase boundary contact of said reference electrode and said preconditioning electrolyte being such that nonspecific exchange of ions between said reference electrolyte of the reference electrode and said preconditioning electrolyte in said closed hollow chamber is possible, maintaining said boundary contact of said preconditioning electrolyte with said measurement electrode and said reference electrode from prepacking by the manufacturer to removal of said preconditioning electrolyte before an analytical measurement, removing said preconditioning electrolyte from said hollow chamber before an analytical measurement, bringing said sample liquid into phase boundary contact with said measurement electrode and said reference electrode, and measuring the voltage between said measurement electrode and said reference electrode.

2. Method according to claim 1, wherein the hollow chamber contains a pad impregnated with the preconditioning electrolyte and said step of removing said preconditioning electrolyte comprises removing said pad.

3. A method according to claim 2, wherein the pad consists of an elastic, absorbent material in which the hollow chamber prepacked by the manufacturer is prepacked by the step of enclosing the pad, prestressed against its elasticity, in the hollow chamber.

4. A method according to claim 2, wherein the pad consists of a viscose sponge material.

5. A method according to claim 4, wherein the viscose-sponge material is a cotton-viscose sponge cloth.

6. A method according to claim 2, which includes the steps of fixing the pad to the closure part and removing the pad therewith.

7. A method according to claim 1, in which at least one of the measurement electrodes includes a lead-off electrolyte, a lead-off contact element and a barrier element arranged on a phase boundary contact surface to the hollow chamber closing off an electrode chamber for the lead-off electrolyte, said barrier element being selectively permeable for certain species of ion, wherein the lead-off electrolyte contains the species of ion to which the barrier element is permeable and in the same activity as the preconditioning electrolyte and providing an electrode arrangement includes the step of closing off the reference electrode in the direction of the hollow chamber by an electrolyte bridge permeable to all species of ions.

8. A method according to claim 1, in which at least one of the measurement electrodes includes a lead-off electrolyte, a lead-off contact element and a barrier element arranged on a phase boundary contact surface to the hollow chamber closing off an electrode chamber for the lead-off electrolyte, said barrier element being selectively permeable for certain species of ion, wherein the lead-off electrolyte contains the species of ion to which the barrier element is permeable and in the same activity as the preconditioning electrolyte and wherein the reference electrode includes a pad held on the base part, said held pad being in phase boundary contact with the lead-off contact and in which providing an electrode arrangement includes the step of impregnating said held pad with the preconditioning electrolyte of the hollow chamber as reference electrolyte.

9. A method in accordance with claim 8, in which providing an electrode arrangement includes laying the removable pad against the pad held on the base part.

10. A method according to claim 11, wherein the hollow chamber is formed by a trough on the base part and providing an electrode arrangement includes providing on the bottom of said trough phase boundary surfaces of the measurement electrode and the reference electrode.

11. A method according to claim 1, in which providing an electrode arrangement includes forming the closure part by a flexible foil jointly covering at least the phase boundary surfaces of the electrodes.

12. A method according to claim 11, in which at least one of the measurement electrodes includes a lead-off electrolyte, a lead-off contact element and a barrier element arranged on a phase boundary contact surface to the hollow chamber closing off an electrode chamber for the lead-off electrolyte, said barrier element being selectively permeable for certain species of ion, wherein the lead-off electrolyte contains the species of ion to which the barrier element is permeable and in the same activity as the preconditioning electrolyte.

13. A method according to claim 1, in which the lead-off contact element of the reference electrode contains elementary copper and the reference electrolyte contains a copper salt and, without an intermediate salt bridge, is adapted to be brought into phase boundary contact with the sample.

14. A method according to claim 13, wherein the concentration of the copper salt in the reference electrolyte is higher than 0.2 mol/litre.

15. A method according to claim 14, wherein the concentration of the copper salt in the reference electrolyte is about 1 mol/litre.

16. A method according to claim 13, wherein the lead-off contact element includes a graphite-copper mixture bound with a binding agent.

17. A method according to claim 16, wherein the lead-off contact element of the measurement electrode consists of the same material as the reference electrode and in which providing an electrode arrangement includes applying the measuring electrode and the reference electrode in the same working step.

18. A method according to claim 13, wherein the lead-off contact element includes a graphite strip which is coated with copper in the region in contact with the reference electrolyte.

19. A method according to claim 1, wherein the reference electrolyte is liquid, the reference electrode is adapted to be brought into phase boundary contact with the liquid to be analyzed by means of an electrolyte bridge preventing the mixing together of sample and reference electrolyte and the electrode chamber connecting the lead-off contact element wherein the electrolyte bridge, filled with the reference electrolyte, is so constructed by sufficiently large dimensioning of the distance and/or sufficiently small dimensioning of the cross-section between the electrolyte bridge and the lead-off contact element that the electrode reaction on the lead-off contact element within the desired measurement time is not impaired by the sample brought into contact with the electrolyte bridge.

20. A method according to claim 19, wherein the electrolyte bridge comprises a cellulose acetate membrane with a pore size of about 1 $\mu$m.

* * * * *